US007365247B2

(12) United States Patent
Levy et al.

(10) Patent No.: US 7,365,247 B2
(45) Date of Patent: Apr. 29, 2008

(54) METHOD OF LARGE SCALE MUTAGENESIS IN TOMATO PLANTS

(75) Inventors: Avraham Levy, Rehovot (IL); Rafael Meissner, Rehovot (IL); Yonatan Elkind, Rehovot (IL)

(73) Assignees: Yeda Research and Development Co., Ltd., Rechovot (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 488 days.

(21) Appl. No.: 10/750,909

(22) Filed: Jan. 5, 2004

(65) Prior Publication Data

US 2004/0244076 A1    Dec. 2, 2004

Related U.S. Application Data

(62) Division of application No. 09/508,379, filed as application No. PCT/IL98/00442 on Sep. 10, 1998, now Pat. No. 6,759,569.

(30) Foreign Application Priority Data

Sep. 11, 1997 (IL) .................................... 121750

(51) Int. Cl.
*A01H 1/00* (2006.01)
*A01H 1/02* (2006.01)
*A01H 1/04* (2006.01)
*A01H 1/06* (2006.01)
*C12N 15/01* (2006.01)

(52) U.S. Cl. .................. 800/317.4; 800/276; 800/260; 800/270; 435/410; 435/411

(58) Field of Classification Search .............. 800/317.4
See application file for complete search history.

(56) References Cited

U.S. PATENT DOCUMENTS

| 4,732,856 A | 3/1988 | Federoff |
| 5,013,658 A | 5/1991 | Dooner et al. |
| 5,149,645 A | 9/1992 | Hoekema et al. |
| 5,225,341 A | 7/1993 | Yoder et al. |
| 5,482,852 A | 1/1996 | Yoder et al. |
| 5,523,520 A * | 6/1996 | Hunsperger et al. ........ 800/260 |
| 5,565,347 A | 10/1996 | Fillatti et al. |
| 5,749,169 A | 5/1998 | Briggs |
| 6,759,569 B1 | 7/2004 | Levy et al. |

FOREIGN PATENT DOCUMENTS

| EP | 0289947 | 9/1988 |
| EP | 0436007 | 7/1990 |
| EP | 0563527 | 6/1993 |
| WO | WO 92/01370 | 6/1992 |
| WO | WO 96/39803 | 12/1996 |
| WO | WO 99/12411 | 3/1999 |

OTHER PUBLICATIONS

Bennett et al (1995. pp. 88-99, In: Genetically Modified Foods. American Chemical Soc., Washington, D.C.).*
Khush et al (1985. Int. Rice Comm. Newsletter 34(2): 11-126).*
Privalov et al (1991. Genetika 27(3):450-457).*
Lahiri et al (1993. Bangladesh J. Bot. 22(2): 167-172).*
Chambers et al. "Melanin-Concentrating Hormone is the Cognate Ligand for the Orphan G-Protein-Coupler Receptor SLC-1", Nature, 400:261, 1999.
Dax et al. "A Random Amplified Polymorphic DNA (RAPD) Molecular Marker for the Tm-2a Gene in Tomato", Euphytica, 74(1/2): 159-163, Abstract.
Goldsbrough et al. "Transposition Mediated Re-Positioning and Subsequent Elimination of Marker Genes from Transgenic Tomato", Bio/Technology, 11: 1286-1291, 1993. Abstract.
Hua et al. "Plant Growth Homostasis is Controlled by the *Arabidopsis* BON! And BAP1 Genes", Genes & Development, 15:2263-2272, 2001.
Meissner et al. "A New Model System for Tomato Genetics", Plant Journal, 12(6), 1465-1472, 1997.
Peng et al. "'Green Revolution' Genes Encode Mutant Gibberellin Response Modulators", Nature, 400: 256-261, 1999.
Yakovleva "Genetic Study of Tomato Mutants with Variable Cell Turgor", Genetika, 11(2): 47-54, 1975. Abstract.
Zeerak et al. "Induced *dwarf* Mutants in Tomato", Journal of Nuclear Agriculture and Biology, 23(4): 209-213, 1994.
Bishop et al. "The Tomato *dwarf* Gene Isolated by Heterologous Transposon Tagging Encodes the first Member of a New Cytochrome P450 Family", The Plant Cell, 8(6):959-969, 1996. Claims: X: 22,26-32, Y: 18-21.
Yoder et al. "Ac Transposition in Transgenic Tomato Plants", Molecular Genetics and Genomics, 213(2-3): 291-296, 1988. Abstract.
Zwaal et al. "Target-Selected Gene Inactivation in *Ceanorhabditis elegans* by Using A Frozen Transposon Inserttion Mutant Bank", Proc. Natl. Acad. Sci. USA, 90: 7431-7435, 1993.
Cooley et al. "Site-Selected Insertional Mutagenesis of Tomato With Maize Ac and Ds Elements", Molecular Genetics and Genomics, 252(1-2): 184-194, 1996. Abstract.
Damasco et al. "Gibberellic Acid Detection of Draft Offtypes in Microspropogated Cavendish Bananas", Australian Journal of Experimental Agricultural, 36(2): 237-241, 1996. Abstract.
Scott et al. "Influence of Pollination Treatments on Fruit Set and Development in Parthenocarpio Tomato", HortScience, 19(6): 874-876, 1984.
Scott et al. "Micro-Tom. A Miniature *dwarf* Tomato", IFAS Circular, 370: 1-6, 1989.
Scott et al. "Micro-Gold Miniature *dwarf* Tomato", HortScience, 30(3): 643-644, 1995. p. 643 1-h col., § 2.
Ballinger et al. "Targeted Gene Mutations in Drosophila", Proc. Natl. Acad.Sci. USA, 86: 9402-9406, 1989.

(Continued)

*Primary Examiner*—Medina A. Ibrahim

(57) ABSTRACT

The present invention relates to a rapid and large-scale production of tomato mutants by utilizing a miniature tomato plant which can be crossed with tomato commercial plants. Mutations are induced in the miniature tomato cultivars and desired mutants are subsequently identified in the resulting mutant tomato population.

6 Claims, 6 Drawing Sheets

OTHER PUBLICATIONS

Bensen et al. "Cloning and Characterization of the Maize An1 Gene", The Plant Cell, 7: 75-84, 1995.
Carroll et al. "Germinal Transpositions of the Maize Element Dissociation From T-DNA Loci in Tomato", Genetics, 139: 407-420, 1995.
Cresse et al. "Mu1-Related Transposable Elements of Maize Preferentially Insert Into Low Copy No. DNA", Genetics, 140: 315-324, 1995.
Federoff et al. "Cloning of the Bronze Locus in Maize by A Simple and Generalizable Procedure Using the Transposable Controlling Element Activator (Ac)", Proc. Natl. Acad. Sci. USA, 81(12): 3825-3829, 1984. Abstract.
Federoff et al. "A Versatile System for Detecting Transposition in *Arabidopsis*", Plant Journal, 3(2): 273-289, 1993. Abstract.
Feinberg et al. "A Technique for Radiolabeling DNA Restriction Endonuclease Fragments to High Specific Activity", Analyses in Biochemistry, 132(1): 6-13, 1983. Abstract.
Fillatti et al. "Efficient Transfer of A Glyphosate Tolerance Gene Into Tomato Using A Binary *Agrobacterium tumefaciens* Vector", Bio/Technology, 5: 726-730, 1987. Abstract.
Gorbunova et al. "Circularized Ac/Ds Transposons: Formation, Structure and Fate", Genetics, 145: 1161-1169, 1997.
Greenblatt "A Chromosome Replication Pattern Deduced From Pericarp Phenotypes Resulting From Movements of the Transposable Element, Modulator, in Maize", Genetics, 108: 471-485, 1984.
Hedden et al. "Gibberellin Biosyntheses: Enzymes Genes and Their Regulation", Annual Review of Plant Physiology and Plant Molecular Biology, 48: 431-460, 1997. Abstract.
Hoekema et al. "A Binary Plant Vector Strategy Based on Separation of Vir- and T-Region of the *Agrobacterium tumefaciens* Ti-Plasmid", Nature, 303: 179-180. 1983. Abstract.
Horsch et al. "A Simple and General Method for Transferring Genes Into Plants", Science, 227(4691): 1229-1231, 1985. Abstract.
Jones et al. "Preferential Transposition of the Maize Element Activator to Linked Chromosomal Locations in Tobacco", The Plant Cell, 2: 701-707, 1990.
Kaiser et al. "'Site-Selected' Transposon Mutagenesis of Drosophila", Proc. Natl. Acad. Sci. USA, 87: 1686-1690, 1990.
Keddie etal. "The DCL Gene of Tomato Is Required for Chloroplast Development and Palisade Cell Morphogenesis in Leaves", The EMBO Journal, 15(16): 4208-4217, 1996.
Knapp et al. "Transgenic Tomato Lines Containing Ds Elements at Defined Genomic Positions as Tools for Targeted Transposon Tagging", Mol. Gen. Genet., 243: 666-673, 1994. p. 666 Right Hand Column: par.1.Abstract. Claims: 33-36.
Leutwiler et al. "The DNA OF *Arabidopsis thaliana*", Molecular Genetics and Genomics, 194(1-2): 15-23, 1984. Abstract.
Mena et al. "Diversification of C-Function Activity in Maize Flower Development", Science, 274(5292): 1537-1540, 1996. Abstract.
Osborne et al. "Ac Transposition From A T-DNA Can Generate Linked and Unlinked Clusters of Insertions in Tomato Genome", Genetics, 129: 833-844, 1991.
Rommens et al. "Characterization of the Ac/Ds Behaviour in Transgenic Tomato Plants Using Plasmid Rescue", Plant Molecular Biology, 20(1): 61-70, 1992. Abstract.
Schoenmakers et al. Isolation and Characterization of Nitrate Recuctase-Deficient Mutants in Tomato (*Lycopersicon esculemtrum* Mill.), Molecular and Gene Genetics, 227: 458-464, 1991. Abstract.
Scott et al. "Adjacent Sequences Influence DNA Repair Accompanying Transposon Excision in Maize", Genetics, 142: 237-246, 1996.
Shalev et al. "The Maize Transposable Element Ac Induces Recombination Between the Donor Site and An Homologous Ectopic Sequence", Genetics, 146: 1143-1151, 1997.
Sundaresan et al. "Pattern of Gene Action in Plant Development Revealed by Enhancer Trap and Gene Trap Transposable Elements", Genes & Development, 9(14): 1797-1810, 1995. Abstract.
Thomas et al. "Analysis of the Chromosomal Distribution of Transposon-Carrying T-DNAs in Tomato Using the Inverse Polymerase Chain Reaction", Molecular Genetics and Genomics, 242(5): 573-585, 1994. Abstract.
Weide et al. "A Simple, Nondestructive Spraying Assay for the Detection of An Active Kanamycin Resistance Gene in Transgenic Tomato Plants", Theoretical Applied Genetics, 78(2): 169-172, 1989. Abstract.
Weigel et al. "A Development Switch Sufficient for Flower Initiation in Diverse Plants", Nature, 377(6549): 495-500, 1995. Abstract.
Wisman et al. "Genetic and Molecular Characterization of Adh-1 Null Mutant in Tomato", Molecular Genetics and Genomics, 226: 120-128, 1991. Abstract.

* cited by examiner

DsG/DsE

Bam35S-Ac

Ds378-GUS

..TTGCGTGACC (Ds378-GUS) GCGTGACCCG..

Ex1 GCGTGAC-    gc    -CGTGACC
Ex2 GCGTGAC-    gg    -CGTGACC

METHOD OF LARGE SCALE MUTAGENESIS IN TOMATO PLANTS

This application is a Divisional Application of U.S. patent application Ser. No. 09/508,379, filed Jun. 8, 2000, now U.S. Pat. No. 6,759,569, which is a National Phase Application of PCT Application No. PCT/IL98/00442, filed Sep. 10, 1998, which claims priority from Israeli Patent Application No. 121750, filed Sep. 11, 1997.

FIELD OF THE INVENTION

The present invention is in the field of plant genetics and relates to improved methods for mutagenesis, gene identification and analysis of gene function in crop plants. The methods are useful in any plant species and their use in tomato is exemplified herein.

BACKGROUND OF THE INVENTION

The genomes of higher plants are estimated to contain 30.000 to 50,000 genes. A function has been ascribed to only a few hundred plant genes. The isolation of new genes, and the mutation of these newly isolated genes, is frequently required to ascertain gene function. Crop improvement through biotechnology depends on detailed characterization of newly isolated genes.

The *Arabidopsis* model system has greatly contributed to the remarkable advances in plant molecular biology during the last decade. The major reasons for the successful use of *Arabidopsis* are its small size, short life cycle and relatively small genome (Leutwiler et al., 1984). Additionally, *Arabidopsis* can be easily transformed with foreign DNA (Bechtold et al., 1993). These features facilitate the genetic dissection of any trait expressed in *Arabidopsis* through screening of large populations of mutants for the various genes, which control a trait of interest. Plant populations mutagenized by ethyl methanesulfonate (EMS), fast neutron bombardment, T-DNA insertions, and transposon tagging have proved invaluable to plant biologists as a means of dissecting the genetic control of plant development and genome traits (Koncz et al., 1992). Despite the considerable advantages of using *Arabidopsis* as a model for genetic analysis, it is not a crop plant, and the knowledge acquired in this species cannot always be applied to other agronomically important crop species. For example, *Arabidopsis* has a silique type of fruit and therefore it is a good model species for fruit development in members of the *Brassicaceae* but is not useful for plants which produce a fleshy, berry-type, fruit.

On the other hand, tomato (*Lycopersicon esculentum*) is a good model for crop species that produce a fleshy, berry-type fruit. Tomato is well known genetically. Tomato has a relatively small diploid genome (n=12, C=1 pg) containing hundreds of mapped traits and molecular markers (Tanskley, 1993). Tomato can be transformed with foreign DNA (McCormick et al., 1986). Moreover, it is one of the most important crops in the fresh vegetable market as well as in the food processing industry (Hille et al., 1989; Rick and Yoder, 1988).

A major obstacle to making further advances in tomato genetics is the lack of large mutant populations required for gene identification. A useful mutant population for tomatoes would contain at least one mutant allele for every tomato gene. Such a population would make it possible to achieve saturated mutagenesis in this crop. Although techniques exist for producing mutant tomato plants, it is currently impractical, due to time and space constraints, to apply these techniques on a sufficiently large scale to obtain populations in which the genome is saturated with mutations. These same constraints limit research in other agronomic crops.

Mutant tomato plants have been produced through the use of DNA damaging agents such as EMS (Hildering and Verkerk, 1965; Schoenmakers et al., 1991; Wisman et al., 1991), X-rays (Hildering and Verkerk. 1965), or fast-neutrons (Verkerk, 1971), although to a much more limited extent compared to similar efforts in *Arabidopsis*. A few hundred mutant tomato lines, available through the Tomato Genetic Resource Center, have been described, but no stocks of mutagenized M2 seeds, originating from a large population of M1 plants, are available for screening mutations in new genes.

Insertional mutagenesis by T-DNA tagging is not practical in tomato as transformation procedures are still laborious. Transposon tagging, on the other hand, is a promising approach for mutagenesis and gene identification in tomato and other agronomic species. The Ac/Ds transposable element family has been shown to be active in tomato (Yoder et al., 1988) and patterns of Ac/Ds transposition in this species have been described (Carroll et al., 1995; Osborne et al., 1991; Rommens et al., 1992; Yoder et al., 1988). Tomato lines have been produced containing Ds elements that were mapped in the tomato genome (Knapp et al., 1994; Thomas et al., 1994). These lines make it possible to take advantage of the preferential insertion of Ac/Ds at nearby sites (Dooner and Belachew, 1989; Jones et al., 1990). The Ac/Ds tagging system was used to tag and isolate several genes, such as cf9, a locus responsible for *Cladosporium* resistance (Jones et al., 1994); dwarf, a gene encoding a cytochrome p450 homolog (Bishop et al., 1996); and dcl which controls chloroplast development (Keddie et al., 1996).

Reverse genetics is an efficient strategy for determining the function of an isolated gene (Benson et al. 1995). In maize, for example, a mutation in a gene of interest can be identified by screening a large plant population composed of 48,000 randomly mutagenized plants. In principle, each plant in this mutant population contains a different mutation caused by insertion of a transposable element. A plant containing the insertion of a transposable element in the gene of interest is identified by polymerase chain reaction (PCR) analysis. A first primer having a nucleotide sequence corresponding to the transposon and a second primer having a nucleotide sequence corresponding to the gene of interest are used in the PCR reaction with DNA isolated from presumptive mutants. In principle, a PCR product is only produced if the transposon is inserted in the gene of interest. Mutant plants comprised of DNA from which a PCR product is produced in the PCR reaction are analyzed to determine the effect of the mutation on plant growth and development and the function of the gene of interest is thereby ascertained.

It is impractical to use reverse genetics in most crop species, however, because it would require considerable time and effort, and extensive field facilities, to produce and accommodate the tens of thousands of T-DNA or transposon-tagged plants that must be grown to maturity to detect the mutant of interest. Accordingly, an alternative strategy is required to make reverse genetics a reality in most crop species. Likewise, a practical method is required to screen large populations of crop plants transformed with a DNA construct capable of detecting a DNA element which controls gene expression such as a promoter or an enhancer.

SUMMARY OF THE INVENTION

It is an object of the present invention to provide improved methods for mutant identification and characterization using a miniaturized crop plant.

It is another object of the present invention to provide improved methods for characterization of cloned nucleotide sequences.

It is yet another object of the present invention to provide improved methods for the cloning of nucleotide sequences.

These objects, and others, are achieved by providing a method for selecting a mutant miniature plant having a desired trait, comprising the steps of:
- (a) providing a population of miniature plants, wherein said miniature plants have the following characteristics: (i) reduced size in comparison to a commercial cultivar of the same species; (ii) maturation to produce viable seeds or tubers at a plant density of at least ten-fold higher than standard growth conditions used for a commercial plant of the same species; and (iii) capable of being crossed with a commercial plant of the same species;
- (b) generating mutant miniature plants in said miniature plant population by treating said miniature plants with a mutation-inducing agent, to produce a mutant plant population; and
- (c) selecting a mutant miniature plant having said desired trait within said mutagenized miniature plant population.

In all aspects and embodiments of the present invention as described herein, the population of miniature plants may be generated by natural or induced mutations, by genetic engineering, or by treatment with plant growth factors. Examples of miniature plants that can be used according to the invention include, but are not limited to, miniature tomato cultivars such as 'Micro-Tom' and 'Micro-Peach'. The mutation-inducing agent used in step (b) above may be a chemical mutagen such as ethyl methanesulfonate (EMS), methyl methane-sulfonate (MMS), methyl-N-nitrosourea (MNU), and bleomycins. Alternatively, the mutation-inducing agent may be irradiation such as UV, γ-irradiation, X-rays, and fast neutrons. Finally, the mutation-inducing agent may be a mobile DNA sequence which is a T-DNA or a transposable element which is selected from the group consisting of an autonomous transposon, a non-autonomous transposon, and an autonomous/non-autonomous transposon system such as, but not being limited to, the maize Ac/Ds transposable element. The commercial plant of the same species is a plant used to produce food, fiber or flowers, including but not being limited to, plants which produce a berry-type fruit such as tomato, grape, prune, eggplant, citrus fruits, and apple, or a plant of the Solanaceae family, e.g. potato.

In another embodiment, the present invention provides a mutant miniature population wherein a miniature plant of said population has the following characteristics: (i) reduced size in comparison to a commercial plant of the same species; (ii) matures to produce viable seeds or tubers at a density of at least ten-fold higher than standard growth conditions used for a commercial cultivar of the same species; (iii) capable of being crossed with a commercial plant of the same species; and (iv) carries a mutation induced by an agent which is a chemical mutagen, irradiation, or a mobile DNA sequence.

Yet another embodiment of the present invention provides a method for identifying a miniature plant containing a mobile DNA sequence inserted into a gene of interest comprising the steps of:
- (a) providing a population of miniature plants, wherein said miniature plants have the following characteristics: (i) reduced size in comparison to a commercial plant of the same species; (ii) maturation to produce viable seeds or tubers at a plant density of at least ten-fold higher than standard growth conditions used for a commercial plant of the same species; and (iii) capable of being crossed with a commercial plant of the same species;
- (b) generating mutant plants in said population of miniature plants by treating said plants with a mobile DNA sequence;
- (c) screening DNA extracted from said mutant plants by PCR using a first primer to a nucleotide sequence corresponding to said mobile DNA sequence and a second primer corresponding to a nucleotide sequence of said gene of interest; and
- (d) identifying a miniature plant comprised of DNA which produces a PCR product in the presence of said first and second primers.

Yet another embodiment of the present invention provides a method for producing a mutant population of a miniature plant comprising the steps of:
- (a) providing a population of miniature plants, wherein said miniature plants have the following characteristics: (i) reduced size in comparison to a commercial plant of the same species; (ii) maturation to produce viable seeds or tubers at a plant density of at least ten-fold higher than standard growth conditions used for a commercial plant of the same species; and (iii) capable of being crossed with a commercial cultivar of the same species; and
- (b) generating said mutant plants in said miniature plant population by treating said miniature plants with a mutation-inducing agent.

When said mutation-inducing agent of step (b) is a T-DNA, the miniature plants are infected with *Agrobacterium*, thus producing multiple transformants wherein each transformant contains a T-DNA insertion in a different genomic position. When said mutation-inducing agent of step (b) is a transposon, the mutant miniature plant population is obtained from the progeny of miniature plants containing an active transposition system. This active transposition system may be a plant native transposon or a transposon introduced into the plant by genetic engineering techniques well known to an artisan in the field, such as an autonomous transposon or a transposable element obtained by crossing a plant containing a non-autonomous transposon with either a transposase source or a plant containing an autonomous transposon. The transposable element is, for example, the maize Ac/Ds transposon system.

Yet another embodiment of the present invention provides a method for identifying a nucleotide sequence which controls plant gene expression comprising the steps of:
- (a) transforming a miniature plant of a crop plant with a DNA construct to produce a population of randomly mutagenized plants, wherein said DNA construct comprises a gene sequence encoding a screenable marker which lacks a promoter or contains a minimal promoter, wherein said miniature plant has the following characteristics: (i) reduced size in comparison to a commercial plant of the same species; (ii) maturation to produce viable seeds or tubers at a plant density of at least ten-fold higher than standard growth conditions used for a commercial plant of the same species; and (iii) capable of being crossed with a commercial cultivar of the same species to produce a population of randomly mutagenized plants;

(b) identifying a miniature plant within said plant population which is transformed with said DNA construct and expresses said screenable marker; and (c) cloning the nucleotide sequence which is operably linked to said gene encoding said screenable marker from the total DNA isolated from said transformed miniature plant identified in step (b).

The screenable marker may be GUS or luciferase, the mobile DNA sequence may be a T-DNA or a transposable element and the nucleotide sequence which controls plant gene expression may be a promoter or an enhancer.

In yet a further embodiment, the invention provides a method for producing a mutant population of a commercial plant with a desired trait, which comprises the steps of:

(a) crossing a mutant miniature plant having said desired trait selected according to the selection method of the present invention, with a commercial plant of the same species; and (b) selecting progeny which resemble the commercial parent plant and express said desired trait.

According to this embodiment, the invention also encompasses mutant populations of commercial plants obtained by the above method.

DETAILED DESCRIPTION OF THE INVENTION

Figure 1:
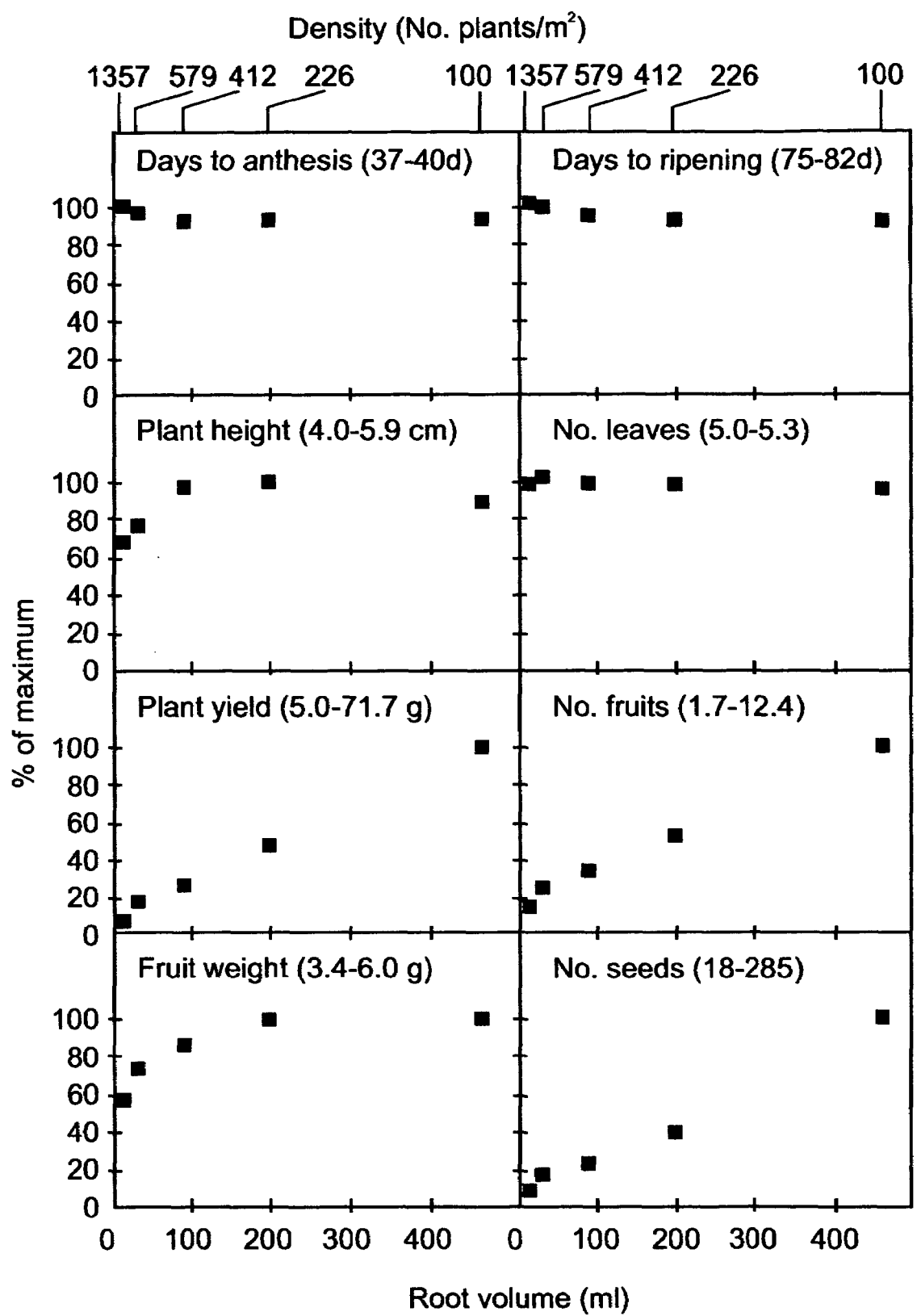
FIG. 1 shows the response of 'Micro-Tom' to different growth conditions.

The present invention enables the rapid and large scale production and efficient screening of mutagenized plants. This is accomplished by utilizing a miniaturized crop plant which can be crossed with a commercial cultivar of the same species. Mutations are induced in the miniature plant, and the mutants subsequently identified in the mutant miniature plant population which can be efficiently grown to maturity at high density.

The major bottleneck to undertaking reverse genetics with most crop species, such as a tomato, is the considerable time, effort and space required to produce and handle very large populations of mutant plants. The present invention enables, for example, the rapid, large-scale production and efficient screening of transposon-mutagenized plants which is otherwise not practical with current production techniques. It is estimated that 100,000 different transposon-mutagenized plants are necessary to produce a representative plant population for reverse genetics of most species of agronomic interest such as a tomato. The production of such a library of mutants in a crop plant can be accomplished with the present invention by means of employing a miniature plant. The invention enables the inactivation of almost any desired gene by identifying a line which carries a transposon inserted in the target gene of interest in a large plant population grown within a manageable planting area. The identification of the transposon insertion in a target gene is done by screening pools of transposon-carrying plants with PCR using one primer having a nucleotide sequence corresponding to the target gene and a second primer having a nucleotide sequence correspond to the transposon. A PCR product is only produced from a DNA substrate isolated from a plant mutant which has the transposon inserted in the gene of interest.

The methods of the present invention are suitable for any plant of agronomic interest including plants used to produce food, fiber or flowers. These agronomic crop plants include, but are not limited to, plants which produce berry-type fruits such as tomato, grape, citrus fruits, prune, apple, eggplant; plants of the Solanaceae family, e.g. potato; and maize as well as flower and fruit tree species.

The methods of the invention will also facilitate identification of genes of commercial value, isolation of new genes, introduction of new genes in classical breeding programs, and isolation of tissue specific promoters and enhancers. Genes of commercial value include genes affecting fruit ripening, and genes improving yield and/or quality of the plant. New genes, which are likely targets of isolation, include genes related to sugar content in the fruit, to mineral uptake, and so on. Tissue specific promoters may be isolated by using a "gene trapping" methodology engineered within the transposon.

Inactivation of almost any desired gene is accomplished by random mutagenesis in the miniature plant by insertion of a mobile DNA sequence such as a transposable element into the plant genome, and identifying a plant which carries a transposon inserted in the target gene. Identification of the insertional mutant of interest is carried out by screening pools of transposon-carrying plants by PCR, using one primer having a nucleotide sequence corresponding to the target gene and a second primer corresponding to the transposon. The miniaturized crop plant population is also utilized for efficient screening and identification of plant promoters.

The terms used in the specification are defined as follows:

A miniature plant, cultivar or crop has an overall size or biomass which is significantly reduced compared to the wild-type crop of the corresponding plant, cultivar or plant. The miniature plant, cultivar or crop can be grown to maturity to produce viable reproductive organs such as fruit, seeds, tubers, etc. at a plant density which is impractical with the corresponding wild-type plant. For example, the miniature plant, cultivar, or crop can be grown to maturity at a plant density of at least 1-fold, preferably 5-fold, 10-fold, 50-fold, 100-fold, 150-fold, 200-fold, 250-fold, 300-fold, or higher, than the standard growth conditions used for a commercial plant of the same species. It is possible to grow a wild-type plant at high density, but only up to the seedling or young plant stage, and no fruits, seeds or tubers are produced. In contrast, the miniature crops of the present invention can be grown at high plant density to maturity with development of mature fruits, seeds, tubers, etc.

Transposon—a natural DNA sequence able to move or "jump" to different locations in the genome. Through insertion into a gene and resulting gene disruption, the transposon causes a mutation in the gene. Transposons have been found in bacteria, Drosophila, yeast, nematodes, plants and mammals.

Transposable element—corresponds to a transposon.

Transposase—protein expressed by an autonomous transposon which binds to the terminal regions of a transposon, and mediates transposon excision and transposition to another location in the genome.

Autonomous Transposon—an element that codes for a transposase and has terminal regions recognized by the transposase for its catalytic activity and thus transposes autonomously. Mutations caused by autonomous transposons are unstable. Examples of autonomous transposons are the Ac (Activator) transposons of maize.

Non-Autonomous Transposon—an element that contains the terminal regions recognized by a transposase but does not code therefor, and thus needs a transposase supplied in trans in order to excise and transpose to another location in the genome. Examples of non-autonomous transposons are the Ds (Dissociation) transposons of maize, that can be used together with an autonomous, e.g. Ac, transposon.

The miniature cultivar of the crop plant may be developed from natural or induced mutations, by genetic engineering or by treatment of the crop plant of interest with plant growth factors. Dwarf mutants are ubiquitous in the plant kingdom and have been found in a large number of species.

One of the most significant set of dwarf genes are the rht (reduced height) genes of wheat (Gale and Youssefian, 1985). These genes are in large part responsible for the green revolution The shorter straw of dwarf cultivars can be "loaded" to higher yields (heavier spikes) per plant, and allow the plants to be grown at a higher density than is possible with tall cultivars, leading to an increase in wheat yields worldwide. The height of a wild type of wheat is about 120-140 cm; it is reduced to 90-100 cm by the presence of one dwarfing gene, to 40-60 cm by the presence of two dwarfing genes. Today, standard wheat cultivars contain one or two dwarfing genes. In these plants, reduced height is not associated with miniaturization of other plant organs (e.g. leaves or spikes) and therefore is not useful for large scale mutagenesis. Extreme dwarf wheat plants, however, could be used for facilitating large scale mutagenesis in this species.

Similarly, dwarfing genes have been found in other cereals such as maize and rice; in legumes such as pea; in vegetables such as pepper, eggplant and tomatoes; in ornamental plants such as roses; and in trees such as oranges and other citrus. The mode of action of these genes varies. Several examples of dwarf plants, the genes responsible, and their mode of action are described in a recent review (Hedden and Kamiya, 1997). For example, some dwarfs are defective in the synthesis of one of the plant hormones (e.g., gibberellin), whereas other dwarfs synthesize gibberellin but are insensitive to it (e.g., GAI=gibberellin insensitive mutants). However, for most dwarf plants, the mode of action is not known. Such dwarf plants, or cloned genes which can be manipulated and considerably reduce plant size, can be exploited for subsequent large-scale mutagenesis in any crop by the claimed invention.

General methods for isolating and characterizing dwarf plants in numerous crops are available. Plants can be transformed with isolated genes which affect overall size. For example, the apetala gene isolated from *Arabidopsis* was used to modify the size of transformed poplar plants. Miniature crops can be constructed through traditional breeding methods. In the case of cultivar 'Micro-Tom', two major genes designated miniature and dwarf are responsible for the miniature phenotype.

Plants of a dwarf or miniature cultivar are grown at a density of at least 10-fold higher than under standard field conditions because the size of the miniature plants is significantly reduced. This facilitates analysis of large plant populations in small areas. In the case of the tomato miniature cultivar 'Micro-Tom', as described in the examples hereinafter, the plants are grown at a density of about 200-fold higher than can be achieved with commercial cultures under standard field conditions. New mutants including insertion mutants obtained in the miniature cultivar can be transferred to a commercial background by standard crosses with the crop by segregating out the miniaturizing gene(s) or transgene(s).

Any mutagenesis technique can be used to obtain miniature cultivars according to the invention including, but not being limited to, chemical treatment, irradiation, or by DNA insertion of T-DNA or transposons from the host plant or from a heterologous origin, using techniques well known to the skilled artisan in this field. Insertional inactivation leading to dwarfism can be achieved by the screening of large plant populations. Chemical treatment for production of mutants of the miniature cultivar can be carried out by known techniques with mutagens such as ethyl methanesulfonate (EMS), methyl methanesulfonate (MMS), methyl-N-nitrosourea (MNU), bleomycin, and the like. Mutation can also be effected by known techniques through irradiation with UV-irradiation, X-rays and fast neutrons (See, for example, Poehlman, 1987 or Malmbery, 1993).

Insertional inactivation of genes with a mobile DNA sequence may be undertaken. The mobile DNA sequence may be a T-DNA or a transposon.

T-DNA mutagenesis may be carried out by known methods via *Agrobacterium* (Hoekema et al., 1983; U.S. Pat. No. 5,149,645) Transposon insertion mutagenesis may be done by well-known methods (Fedoroff et al., 1984; U.S. Pat. Nos. 4,732,856 and 5,013,658). The transposable element may be an autonomous transposon, a non-autonomous transposon, or an autonomous/non-autonomous transposon system, e.g. the maize Ac/Ds transposon system.

Large populations of plants, preferably at least thousands of plants, are screened for mutants. Identification of mutants can be done visually, for example, to identify miniature selections. Additional strategies can be used to identify other types of mutants; for example, assaying for specific traits which include, but are not limited to, response to hormones, to minerals, to pathogens, to herbicides, and the like, by known techniques used in plant biology.

Identification of insertional events in a specific gene of interest is accomplished by methods involving PCR screening with a first primer corresponding to a nucleotide sequence of the transposon or of the T-DNA, and a second primer corresponding to a nucleotide sequence of the gene of interest. The gene of interest may be an isolated gene, which has been sequenced in part, or in a whole. Alternatively, the gene of interest may be an expressed sequence tag (EST). PCR methodology is well known in the art. A general description of PCR appears in Delidow et al., 1993. Design of suitable oligonucleotide primer sequences for the PCR method is described by Rychlick et al (1993). Methods for the detection of PCR products is described by Allen et al. (1993).

The plant is identified from which DNA was isolated that produces a PCR product with the first and second primer.

This plant is analyzed to determine the effect of transposon insertion on the phenotype of the plant.

The methods of the present invention can be used to identify and characterize any gene of interest including developmental or disease resistance genes. Sufficient nucleotide sequence of the gene of interest is required for design of a primer for PCR analysis. Once genes of particular interest have been identified, they can be transferred to appropriate commercial backgrounds by techniques well known in plant breeding (see, for example, Poehlman, J M, *Breeding Field Crops*, New York, 1987). The particular strategy utilized will depend upon the crop plant.

The present invention was used to develop a library of mutants in the crop plant tomato. This library greatly enhances the study of tomato genetics and the ability to isolate important genes. This mutant tomato library is based on the miniature-dwarf-determinate *Lypersicon esculentum* cultivar, designated 'Micro-Tom' (Micro tomato), originally bred for home gardening purposes (Scott and Harbaugh, 1989). This cultivar is particularly useful in the present invention because it can be grown at high density, up to 1357 plants per square meter, and it sets fruit when grown at such high densities. Furthermore, the cultivar has a short life cycle, yielding mature fruits within 70-90 days from sowing, which facilitates screening up to four generations per year. These attributes make it an efficient system for screening large mutagenized plant populations and renders saturated mutagenesis in tomato possible.

In addition, the cultivar can be easily and efficiently transformed. Transformation frequencies of up to 80% are obtained with *Agrobacterium*-mediated transformation of cotyledons, and only about 100 days are required from the inoculation of the cotyledons to the harvest of transgenic fruit. Moreover, the cultivar differs from the standard tomato cultivars by only two major genes. Because the two genes controlling the size of 'Micro-Tom' are recessive, dominant traits can be analyzed in a standard background in the F1 generation. One more generation is required to transfer recessive genes to a standard background. Therefore, any mutation or transgene can be conveniently studied in 'Micro-Tom's genetic background, and when needed, transferred into a standard background, using traditional breeding techniques well known to the skilled artisan in this field.

We have also determined that the Ac/Ds transposon tagging system can be used in another miniature tomato, cultivar designated 'Micro-Peach'. 'Micro-Peach' is similar in size to 'Micro-Tom'. However, 'Micro-Peach' has a peach fruit color instead of the red fruit color of 'Micro-Tom'. The Ac/Ds transposon system is very active in 'Micro-Peach' allowing large-scale mutagenesis and reverse genetics.

In order to evaluate 'Micro-Tom' as a model system for mutagenesis and reverse genetics, the growth conditions and transformation conditions for this cultivar were optimized. Subsequently, the screening of 20.000 EMS-mutagenized M2 plants derived from 9,000 M1 individuals was carried out. Mutants with altered pigmentation or modified shape of leaves, flowers and of fruits were found. An Ac/Ds transposable element enhancer trap system (Fedoroff and Smith, 1993) and a gene trap system (Sunadaresan et al., 1995) were introduced into 'Micro-Tom' and determined to be active. Thus, utilization of the 'Micro-Tom' cultivar can achieve the goals of saturated mutagenesis in tomato, or of tagging or insertional inactivation of any gene. The methods of the present invention can be used in any miniature selection of a plant species of interest to aid in the rapid and efficient characterization of genes.

The advantages of the present invention are underscored by the observation that a M2 plant population derived from EMS-mutagenized 'Micro-Tom' consisting of 14.000 individuals, was grown on only 100 m$^2$ of space. Moreover, the work of only one person over a short six month period (M1 was grown in the spring and M2 in the summer of the same year) was required to produce this population. A large number of mutants were recovered, even though the EMS mutagenesis employed was relatively mild, as evidenced by the fact that less than 1% albino plants were found. It is likely that many additional mutant genes are present in the resulting M2 population, which compares favorably with the limited few hundred tomato mutants reported to date by other researchers.

All the M2 families that were derived from individual M1 plants and showed a mutant phenotype, segregated in a 3:1 (dominant: recessive) ratio. This suggests that in 'Micro-Tom', under the experimental conditions used herein, gametes are derived from a single cell present in the embryo of the mature seed at the time of mutagenesis. These data are in agreement with previous reports (Hildering and Verkerk, 1965; Verkerk, 1971), suggesting that between one to three cells give rise to the sporocyte in mutated tomato plants.

Although transposon tagging systems have been previously described in tomato (Carroll et al., 1995; Knapp et al., 1994; Rommens et al., 1992; Yoder et al., 1988), there is no previous report in the literature of an enhancer and gene trapping system for this plant. However, also according to the present invention, two systems for selection of unlinked transpositions were introduced into tomato: one system based on NAM sensitivity and kanamycin resistance (Sundaresan et al., 1995), and a second system based on the excision-insertion selection (Fedoroff and Smith, 1993), which takes advantage of the efficient detection of the hygromycin resistance contained within Ds. In addition, using the resistance to chlorosulfuron as an excision marker, coupled with other agronomic features of 'Micro-Tom', a large population of presumptive mutants can be screened for enhancers and promoters and used for gene isolation. Furthermore, the recently described approach for site-selected insertions in somatic tissues of tomato (Cooley et al., 1996) can also be applied in 'Micro-Tom' for stable germinal transposition events. In this respect, the Ac/Ds system shown to be active in 'Micro-Tom' can also contribute to reverse genetics via gene knockout or insertional inactivation.

Thus by means of the present invention, 'Micro-Tom' was used to develop a model system for genetic studies in plants. It accelerates the characterization of transgenic plants, and facilitates the isolation of mutants, promoters and genes. 'Micro-Tom' can be used as a general model system for other commercially important crops (e.g. citrus, grapes. etc.) that produce berry-type fruit. Any fruit gene, promoter, and mutant found in 'Micro-Tom' can facilitate the study of genetics, physiology and metabolism of other botanically similar fruits. Likewise, 'Micro-Tom' can be used as a general model system for study of plant developmental mutants and genes as well as other important agronomic loci. The methods of gene identification and characterization efficiently used with the miniature tomato cultivar 'Micro-Tom' can be readily employed with other dwarf mutants in other plants including agronomically important crop species.

The following examples are provided for illustration and are not to be construed as a limitation upon the claims. It will occur to those of ordinary skill in the art that various modifications may be made to the disclosed embodiments and that such modifications are intended to be within the scope of the present invention. All publications and patent applications mentioned in this specification are indicative of the level of skill of those in the art to which the invention pertains. All publications and parent applications are herein incorporated by reference to the same extent as if each individual publication or patent application were specifically and individually indicated to be incorporated by reference in its entirety.

EXAMPLES

Example 1

Growth Habit and Genetic Makeup (a) Methods: 'Micro-Tom' plant seeds were sown and grown up to fruit maturity in nursery travs or pots. For the plant density experiment, each treatment corresponded to growth in a different root volume. For that purpose, plants were grown in commercial nursery compartmentalized trays of 13, 33, 90 or 200 ml, or in pots of 465 ml capacity. There were two replications in each treatment, each consisting of 84 (13 ml treatment), 72 (33 ml), 63 (90 ml), 50 (200 ml) and 15 (465 ml) plants that were analyzed for each trait.

(b) Results: 'Micro-Tom' plants were grown from seeds through fruit maturation in nursery trays with root compartments of various sizes to determine the effect of density on plant growth as well as on fruit and seed maturation. Densities of 100 to 1357 plants per $m^2$, equivalent to root volumes ranging from 465 to 13 ml, were tested. The response of 'Micro Tom' to different growth conditions is shown in FIG. 1. The growth traits examined are indicated in each box with the range of values (minimum-maximum) given in parenthesis. Each trait, given as percentage of the maximum value for this trait is expressed as function of the root volume (bottom scale), or of the plant density (upper scale). The following traits were measured: Days to anthesis (the average number of days from sowing to anthesis); days to ripening (the average number of days from sowing to fruit color turning); plant height (the height (in cm) from the soil surface to the first inflorescence); number of leaves (the number of leaves on the main stem); plant yield (the total fruit weight (in g) per plant); number of fruits (the number of fruits per plant); fruit weight (the average (in g) of a fruit); and number of seeds (the average number of seeds per plant). Error bars were too small to be indicated.

Some traits were barely affected by plant density. For example, the number of days from seed sowing to anthesis ranged from 37 to 40 days, and the number of days from seed sowing to fruit ripening ranged from 75 to 82 days. When a control standard determinate tomato cultivar (cv. UC82) was grown under similar conditions, it failed to set fruit at the high densities (412-1357 plants/$m^2$), and it developed fruits only in some of the plants at lower densities (100-226 plants/$m^2$). Other traits, such as plant yield, number of fruits, or number of seeds per plant, responded linearly to changes in plant density with a more than ten-fold difference between the minimum and maximum values obtained in the experiment. The traits of average fruit weight and plant height showed a lesser response to density with a two-fold difference between minimum and maximum values.

Figure 2A:
FIG. 2 shows 'Micro-Tom' wild-type and mutant phenotypes.
Figure 2B:
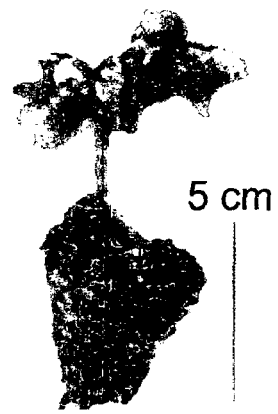

Mature plants grown under the various density levels are shown in FIGS. 2A and 2B. FIG. 2A depicts 'Micro Tom' plants grown in nursery trays with a root compartment of 13 ml (top left), 33 ml (top right), 90 ml (bottom left), and 200 ml (bottom right). FIG. 2B depicts a wild-type 'Micro Tom' mature plant, grown in a 90 ml compartment, with a scale bar. The plant is 5-6 cm tall (not including roots) and fruits have a diameter of 1.5 to 2 cm. 'Micro Tom' plants were grown at a density of 226 plants/$m^2$ in a nursery. Note that in 'Micro-Tom', all plant organs are reduced in size in a well-proportioned manner (with the exception of seeds, which are near-normal in size). This contrasts with other tomato dwarf mutants which are compact in appearance and have large leaves compared to the overall plant size.

These results demonstrate that the dwarf cultivar 'Micro Tom' can be routinely grown at densities of up to 1357 plants/$m^2$ for use according to the invention.

'Micro-Tom' was crossed with UC82, a determinate cultivar, and with VF86, an indeterminate cultivar. The F1 plants of both crosses were very similar in height to the "tall" parent, indicating that the genes responsible for the 'Micro-Tom' type are recessive. In the F2 progeny from the cross with UC82, there was a wide range of growth habit phenotypes. Six out of the 176 F2 plants analyzed were clearly out of the 'Micro-Tom' type, suggesting that it is controlled by two major recessive genes with the possible additional effect of modifiers. Based on the pedigree of 'Micro-Tom' (Scott and Harbaugh, 1989), it appears that dwarf and miniature are the two genes involved in the 'Micro-Tom' phenotype.

These results indicate that the dwarf cultivar 'Micro-Tom' can be easily crossed to a commercial cultivar of tomato.

Example 2

EMS Mutagenesis (a) Methods: For the EMS experiment, plants were grown as described in Example 1, with the exception that the plants were grown in an insect-proof nethouse at the Weizmann Institute of Science, Rehovot, Israel, instead of in a greenhouse.

EMS-mutagenesis was performed on 15,000 'Micro-Tom' seeds. The seeds subjected to mutagenesis and the plants germinated from the mutagenized seeds are designated the M1 generation. The seeds were imbibed for 9 hours on wet Whatman paper in Petri dishes, transferred to an Erlenmeyer bottle containing 150 ml of an unbuffered 0.7% EMS (Sigma) solution. and incubated overnight for 16 hours at room temperature (22° C.) with gentle shaking. Mutagenized seeds were extensively washed, fan dried and sown on the same day in seedling trays. Compared to the control group, the mutagenized seedlings were retarded in their growth, and the percent of germination was reduced by about 25%. Approximately 10% of the M1 plants were sterile. M2 seeds were harvested from 9000 M1 plants. From 70 M1 plants, M2 seeds were harvested individually from each plant, and 10-20 M2 plants were grown for each M1 plant in progeny rows. The rest of the M2 seeds were harvested in bulk, pooling one fruit from each M1 plant. Approximately 20,000 M2 seeds from the bulk harvest were sown and gave rise to 14,000 fruit-producing M2 plants. M3 seeds were harvested in bulk.

(b) Results: In the M1 population (the treated generation), about 1% of the plants showed chlorophyll variegation.

Figure 2C:
Figure 2D:
Figure 2E:
Figure 2F:
Figure 2G:

In the M2 population, a total of 14,000 plants were grown in nursery travs and screened for mutant phenotypes, as shown in FIG. 2C. FIGS. 2D-H depict EMS-generated M2 plants with a mutant phenotype. Out of this population, 111 chlorophyll mutants were found, including albinos, yellow (xanthophyll-like) and light green leaves; FIG. 2G depicts an M2 plant with a chlorophyll mutant phenotype (yellow leaves). Plants with a modified leaf shape, flower (petals) and fruit pigmentation were also observed. Compared to the wild-type round shape fruit, six plants showed an altered fruit shape in all their fruits, including phenotypes such as persimmon shape (FIG. 2D) and pear-shape (FIG. 2E). Plants with oblong fruits had also long and narrow leaves (FIG. 2F).

Figure 2H:

Seventy M2 families derived from individual M1 plants were also screened for mutations. In five families, a mutant phenotype was observed that invariably segregated in a 3:1 ratio. One such family segregated for anthocyanin (purple) pigmentation in the leaves; this family, which is depicted in FIG. 2H, is derived from a single M2 plant and segregated at a 3:1 ratio for anthocyanin.

Example 3

Transposon Tagging and Enhancer Trapping in 'Micro-Tom'

(a) Methods: 'Micro Tom' plants were transformed as described with the following constructs; the transgenic plants were then grown as described in Example 1 in greenhouses.

Figure 3:
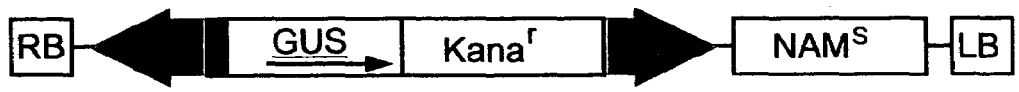
FIG. 3 shows a schematic representation of constructs transformed into 'Micro-Tom'.
Figure 3:
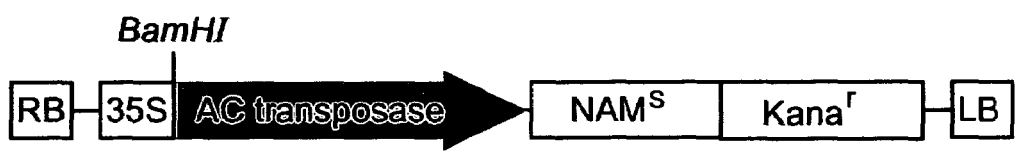
Figure 3:
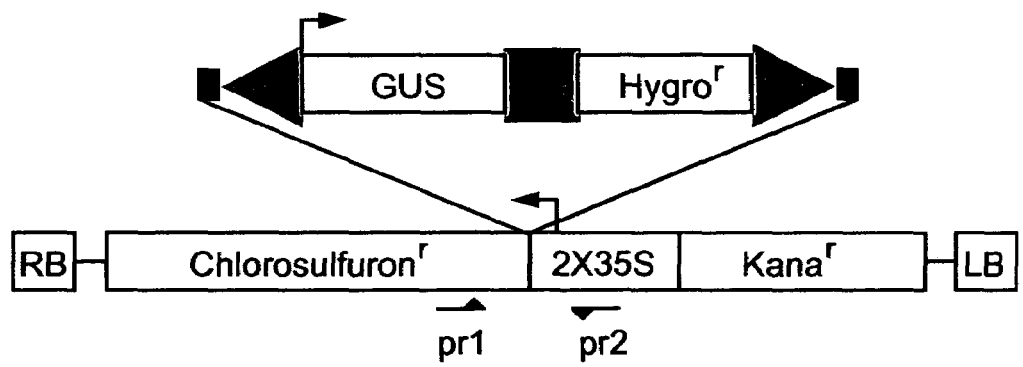

(1) Constructs: Constructs Bam35S-Ac and Ds378-GUS, which were used for enhancer trapping (Fedoroff and Smith, 1993), were obtained from Nina Fedoroff. Constructs DsG and DsE (Sundaresan et al., 1995), which were used for gene trapping and enhancer trapping, respectively, (Sundaresan et al., 1995), were obtained from Venkatesan Sundaresan. These constructs are depicted in FIG. 3, and are described as follows.

Sequences similar to Ac are shown in gray, with the terminal inverted repeats shown as gray arrows. Constructs are flanked by the right (RB) and left (LB) borders of their respective T-DNA. The β-Glucuronidase gene (GUS) is fused to Ac weak promoter in Ds378-GUS, to either the minimal −1 to −46 promoter region (black box) of the 35S in DsE, or to an *Arabidopsis* intron followed by three acceptor splice sites (black box) in DsG (Sundaresan et al. 1995). Resistance to kanamycin (Kan$^r$) or hygromycin (Hyg$^r$) is conferred by the neomycin phosphotransferase or aminocyclitol phosphotransferase genes, respectively. Sensitivity to naphthalene acetamide (NAM$^s$) is conferred by the indole acetic hydrolase gene.

Ds mobility is achieved by crossing the Ds-containing plants (DsG, DsE and Ds378-GUS) with a transposase-producing plant transformed with Bam35S-Ac. In this construct, Ac transposase is produced under the control of the 35S promoter fused to an Ac element whose 5' terminal region, up to the unique BamHI site has been deleted. Chlorsulfuron resistance (Chl$^r$) is obtained upon excision of the Ds element from the Ds378-GUS-containing construct and activation of a mutated acetolactate synthase gene from GUS-containing construct and activation of a mutated acetolactate synthase gene from *Arabidopsis* (Fedoroff and Smith, 1993). Excision footprints (Ex1 and Ex2 SEQ ID NO's:3 and 4 respectively) were obtained upon excision of Ds378-GUS in the F1 of crosses between Bam35S-Ac and Ds378-GUS and amplified with primers pr1 (SEQ ID NO:2) and pr2 (SEQ ID NO:1). The sequence flanking Ds378-GUS is shown above Ex1 and Ex2. The underlined sequence indicates the host duplication flanking Ac insertion site in the original wx-m7 maize allele from which Ds378-GUS was derived.

(2) Transformation: 'Micro-Tom' was transformed with constructs Ds378-GUS, Bam35S-Ac, DsE, and DsG using the following optimized protocol. Plates containing KCMS medium (Fillati et al., 1987) supplemented with 0.2 µg/ml 2,4-D and a tobacco feeder cells layer (Horsch et al., 1985) were incubated at 25° C. under low light conditions for 24 hrs. Cotyledons of seven-day-old seedlings were cut near the petiole and at the tip, laid on a plate, and preincubated for 24 hrs at 25° C. under low light conditions. The concentration of *Agrobacterium* strain LBA 4404 used for co-cultivation ranged from $5 \times 10^7$ to $9 \times 10^7$ cfu/ml, corresponding to an OD ranging from 0.4 to 0.5. Co-cultivation was carried out under the same conditions as preincubation and lasted for 48 hrs. Subsequently, the cotyledons were transferred to 2Z medium (Fillati et al., 1987) containing 100 µg/ml kanamycin and 400 µg/ml carbenicillin for 3-4 weeks, and then transferred again to IZ medium with 200 µg/ml carbenicillin for 2-3 weeks. Shoots were then excised from the cotyledons and transferred to a rooting medium (MSSV) (Fillati et al., 1987) supplemented with 2 µg/ml IBA, 50 µg/ml kanamycin, and 100 µg/ml carbenicillin. Plantlets with roots appeared after 1-3 weeks and were then transferred to the greenhouse.

(3) Selection markers and GUS reporter. In addition to the kanamycin selection needed for transformation and the GUS reporter utilized in the trapping systems, a number of markers were used to select for transposition events (Fedoroff and Smith, 1993; Sundaresan et al., 1995). To that end, sterilized seeds were germinated and grown in 0.8% agar-containing Nitsh medium supplemented with either one or a combination of the following compounds: 20 µg/ml hygromycin (Calbiochem); 0.25 µg/ml naphthalene acetamide (NAM, Sigma); and 100 p.p.b. or 2 p.m. chlorsulfuron (DuPont). GUS staining was done according to Jefferson (1987) and tissue clearing was done according to Beeckman and Engler (1994).

(4) DNA analysis. DNA was extracted from young leaves by the Dellaporta method (Dellaporta et al., 1983), with an additional phenol chloroform extraction. PCR reactions were performed using Promega Taq polymerase according to conditions recommended by the manufacturers, with 2.5 mM $MgCl_2$, and 200 µM dNTPs in an MJ thermocycler. The following program was used: 2 min denaturation at 94° C. and 30 cycles of 1 min at 94° C., 45 min at 55° C., 1 min at 72° C., and a final step of 5 min at 72° C. The primers used to amplify Ds excision products were: pr2, 5' GGATAGTGGGAT-TGTGCGTC 3' (SEQ ID NO:1), which is complementary to sequences in the 35S promoter, and prl, 5' GGATGATTTGTTGGGGTTTA 3' (SEQ ID NO:2), which is complementary to sequences in the ALS gene (FIG. 3). Bands of the expected size for excision products (ca. 322 bp) were extracted from the agarose gel, and DNA was purified using GenClean according to the manufacturer's instructions. These PCR products were cloned into a pGEM-T vector (Promega) and sequenced using the T7 or SP6 primers. For Southern analysis, 2 of µg genomic DNA was digested with HindIII, fractionated on 0.8% agarose gels, and transferred to a nitrocellulose membrane purchased from MSI. Hybridization was performed according to manufacturer's instructions. An internal GUS fragment of 1 kb was amplified by PCR, radiolabeled by the random priming method (Feinberg and Vogelstein, 1983), and used as a probe for Ds detection.

(b) Results: Constructs Ds378-GUS, Bam35S-Ac, DsE, and DsG were transformed into 'Micro-Tom' as described.

Figure 4A:
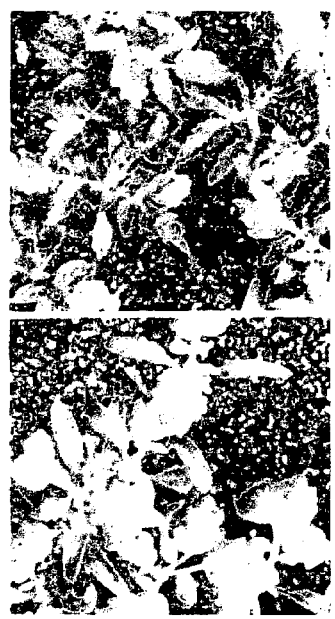
FIG. 4 shows the results of selecting those plants which contain markers used for transposition selection.

These constructs contain the NPTII gene which confers resistance to kanamycin. NPTII can be used as a transformation marker to detect the presence of the T-DNA and to map Ds elements relative to their donor site in Ds378-GUS, or for the selection of unlinked transposition events with DsE and DsG. One advantage of this gene is its use as a non-destructive reporter in whole tomato plants. Spraying 'Micro-Tom' plants at most developmental stages, with 300 µg/ml kanamycin on three successive days, as previously described (Weide et al., 1989), allows identification of kanamycin-sensitive plants without their destruction. In such plants, the young leaves next to the shoot tip become white shortly after spraying, as shown in FIG. 4. FIG. 4A depicts three-week-old 'Micro-Tom' plants following three spray treatments (one per day) with 300 µg/ml kanamycin. Kanamycin-resistant plants, transformed with Bam35S-Ac (top panel) were compared to wild-type, sensitive plants of the same age (bottom panel). White leaves develop at the shoot tip in sensitive plants. Eventually, these leaves die but the subsequently emerging leaves are green and the plant survives.

Figure 4B:

The hygromycin resistance gene indicates the presence of Ds378-GUS, as shown in FIG. 4B. Plants transformed with Ds378-GUS are resistant to 20 µg/ml hygromycin (FIG. 4B, left) while wild-type 'Micro-Tom' is sensitive (FIG. 4B, bottom right).

The indole acetic hydrolase (iaaH) gene confers sensitivity to NAM. Sensitive plants develop a callus-like tissue at the root base and die about three weeks after germination, as shown in FIG. 4C. Plants, transformed with Bam35S-Ac are sensitive to 0.25 µg/ml naphthalene acetamide (FIG. 4C, left) while the wild-type is resistant (FIG. 4C, right). NAM sensitivity can be used as a negative selection marker to select against Bam35S-Ac, thus stabilizing new insertions, and/or to select against the donor site in DsE and DsG.

Figure 4D:
Figure 4C:
Figures 4E, 4F:

The ALS gene confers low resistance to 100 ppb chlorosulfuron in plants carrying an unexcised Ds element, and confers resistance to 2 ppm chlorosulfuron in plants where Ds is excised, as shown in FIG. 4D. Wild-type plants grown on 100 ppb. chlorosulfuron are sensitive (FIG. 4D. left), while plants transformed with Ds378-GUS have low resistance (FIG. 4D. middle).

The results of selecting for the markers used for transposition selection are shown in FIG. 4. X-Gluc staining of F1 (Ds X transposase) plants shows blue sectors (FIG. 4E-F). The promoter-less GUS reporter gene, in DsG, was activated as seen by the blue color in the root of a ten-day old F1 seedling (FIG. 4E). Young fruits, two weeks after anthesis and 1 cm large in diameter, were stained for GUS activity (FIG. 4F). No GUS activity was obtained in negative control plants such as the wild-type or the Bam35S-Ac parent (FIG. 4F, top). GUS was activated in some of the F1 fruits (FIG. 4F, bottom).

Thus, all of the selection features previously described for *Arabidopsis* (Fedoroff and Smith, 1993; Sundaresan et al., 1995) are also applicable to 'Micro-Tom' and therefore can be used for a transposon tagging system. The strategy for generating unlinked and stabilized transposition of Ds, and the strategy for selection of excision and reinsertion, where linked transposition events are most often recovered, have been previously described and compared (Sundaresan, 1996).

Using Ds378-GUS and Bam35S-Ac constructs, a new feature of the excision/reinsertion system results from its ability to identify and rescue kanamycin sensitive plants (FIG. 4A). Following crosses between Ds378-GUS- and Bam35S-Ac-carrying parents, selection of F2 plants for hygromycin resistance and kanamycin sensitivity enables the selection of unlinked, stabilized transposition events, as shown in FIG. 4D. F2 plants (Bam35S-Ac X Ds378-GUS), in which a germinal Ds excision event occurred, are fully resistant to chlorosulfuron (FIG. 4D, right). This feature makes the system developed by Fedoroff and Smith (1993) applicable to tomatoes. This dual system is suitable for selection of both linked and unlinked transposition.

The use of this system in tomato involves first, the selection of Hyg$^r$ and Kan$^s$ plants, which permits the identification of unlinked, stable transposition events. For this group of plants, NAM selection is unnecessary and chlorosulfuron should not be used, as the T-DNA containing the empty donor site segregates away. Second, the selection for plants resistant to chlorosulfuron among the Hyg$^r$ and Kan$^r$ plants permits the identification of linked transposition events. This group of plants is enriched in such events because of the natural tendency for Ac to transpose nearby, and because of some of the unlinked transposition events described above (Hyg$^r$, Kan$^s$ and Chl$^s$ plants) are eliminated.

The activity of the Ac/Ds system introduced into 'Micro-Tom' was confirmed in F1 plants of a cross between transgenic plants transformed separately with Ds378-GUS and Bam35S-Ac by sequencing Ds excision footprints. These footprints, shown in FIG. 3 below the Ds378-GUS construct, are typical of what is expected for Ac/Ds. Out of four clones analyzed, three had the same preferred footprint (GC inversion) as generated by Ac in the wx-m 7 allele of maize or in *Arabidopsis* (C. Weil, personal communication) and tobacco (Gorbunova and Levy, 1997; Shalev and Levy, 1997). These results suggest that preferential footprint formation, as described previously by Scott et al., 1996, is species independent. In addition, GUS staining patterns in F1 plants found in roots of DsG X Bam35S-Ac (FIG. 4E), in leaves (not shown) or in young fruits of Ds378-GUS X Barn35S-Ac (FIG. 4F) indicated reintegration of Ds in or near genes in the course of plant development. In the Ds378-GUS parent, which has the weak Ac promoter, a faint GUS activity was detected only in the immature seeds of young fruits.

Figure 5:
FIG. 5 shows the results of a Southern blot of chlorosulfuron-resistant ($Chl^r$) and hygromycin-resistant ($Hyg^r$) plants.

Finally, transposition was confirmed in Southern blot analysis of chlorosulfuron and hygromycin resistant F2 plants which are the progeny of the cross Ds378-GUS X Bam35S-Ac, as depicted in FIG. 5. Genomic DNA was extracted from: a transgenic plant homozygous for the Ds378-GUS construct (lane a); a plant homozygous for the Barn 35S-GUS construct (lane b); the F1 plant of the cross between these two plants (lane c); and the derived F2 plants which were resistant to 2 ppm chlorosulfuron and to hygromycin (lanes d-l). DNA was digested with HindIII and run on a 0.8% agarose gel, transferred to a nylon membrane and hybridized to an internal 1 kb GUS probe. The arrow points to the 8 kb band from the Barn 35S-GUS parent.

Treatment of DNA from the Ds-containing parent Ds378-GUS digested with HindIII cuts the junction between the 5' end of Ds and the 5' of the GUS gene and does not cut the T-DNA towards the left border (FIG. 3). The GUS probe, present within Ds, revealed a single 8 kb band for the Ds parent (lane a), indicating that a single T-DNA copy is inserted in the genome. No hybridization was obtained, as expected, with the transposase parent (lane b). F2 plants showed variable hybridization patterns (FIG. 5, lanes d-l) indicating element excision and reinsertion at new locations. Analysis of F2 plants from a cross between Ds378-GUS and Bam35S-Ac indicated that out of 22 plants tested for chlorosulfuron resistance, 11 were resistant to hygromycin as evidenced by vigorous root development when incubated on hygromycin-containing medium. This makes the percentage of loss of excised Ac about 50%. which is similar to previously reported figures for maize (Dooner and Belachew, 1989; Greenblatt, 1984; McClintock, 1956), tobacco (Jones et al., 1990), and *Arabidopsis* (Altmann et al., 1992).

Example 4

Reverse Genetics in a Miniature Crop Cultivar

The miniature tomato cultivar 'Micro-Tom' was selected to produce a population of transposon-containing plants. 'Micro-Tom' was transformed with plasmid Bam35S-Ac, depicted in FIG. 3, by the transformation method described in Example 3. Transformants were selfed to produce the first parent plant (line R2-1-1) which is homozygous for plasmid Bam35S-Ac and expresses transposase activity. Plasmids Ds378-GUS, depicted in FIG. 3, and Ds-LUC, depicted in FIG. 6, were transformed into 'Micro-Tom' as described in Example 3. Transformants were selfed to give rise to a series of plants which contained a donor Ds in the T-DNA. The transposase and the Ds plants were crossed to produce F1 seeds. The F1 plants were grown without selection and selfed to produce F2 seeds. F2 seeds were selected for a stable transposition event by growing F2 seedlings in an agar-based medium containing chlorosulfuron, hygromycin and NAM, as described in Example 3. F2 plants, corresponding to independent transposition events, were grown and screened for dominant mutations. F2 plants were selfed and F3 families, each family consisting of 12 F3 plants derived from a single F2 plant, were screened for recessive mutations.

A mutant miniature plant containing a Ds insertion into a known nucleotide sequence (the target) was identified. DNA was extracted from leaves of F2 plants. These DNA samples were subjected to PCR by screening with a first primer corresponding to a nucleotide sequence of the transposon Ds, and a second primer corresponding to the nucleotide sequence of the target nucleotide sequence. The plant that produced a PCR product with the first and second primers was identified and analyzed to determine the effect of transposon insertion into the nucleotide sequence of interest on the phenotype of the plant.

Example 5

Ds-Luciferase

Figure 6:
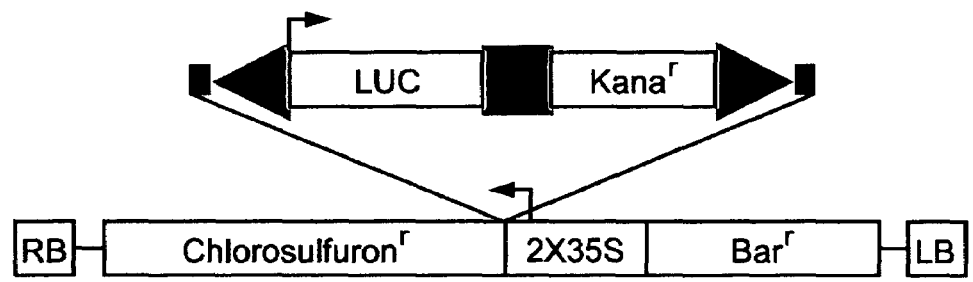
FIG. 6 shows a schematic representation of the plamid Ds-Luciferase (Ds-LUC).

The DNA construct for gene trapping designated Ds-Luciferase is shown in FIG. 6. Sequences similar to Ac are shown in gray with the terminal inverted repeats shown as gray arrows. Constructs are flanked by the right (RB) and left (LB) borders of their respective T-DNA. The luciferase gene (LUC) is fused to Ac left terminus, from nucleotide 1 to 252. This region contains the terminal inverted repeat but lacks a promoter. Resistance to kanamycin (Kan$^r$) or hygromycin is conferred by the neomycin phosphotransferase or aminocyclitol phosphotransferase gene, Chlorosulfuron resistance (Chlorosulfuron[1]) is obtained upon excision of the Ds element from the Ds378-GUS-containing construct and activation of a mutated acetolactate synthase gene from *Arabidopsis* (Federoff and Smith, 1993) by the 35S promoter. The BAR gene confers resistance to the herbicide Basta.

The plasmid Ds-Luciferase was constructed as follows: The Ds element in Ds 378-GUS (FIG. 3) was replaced by the Ds element described above and depicted in FIG. 6, which contains both Luciferase and the kanamycin resistance gene between the Ac borders. Then the 35S promoter-Ds-ALS Asp718 fragment was cloned into binary vector SLJ525 (obtained from Dr. Jonathan Jones, Norwich, UK). The plasmid Ds-Luciferase was transformed into the miniature tomato cultivar 'Micro-Tom' as described in example 3.

Figure 7:
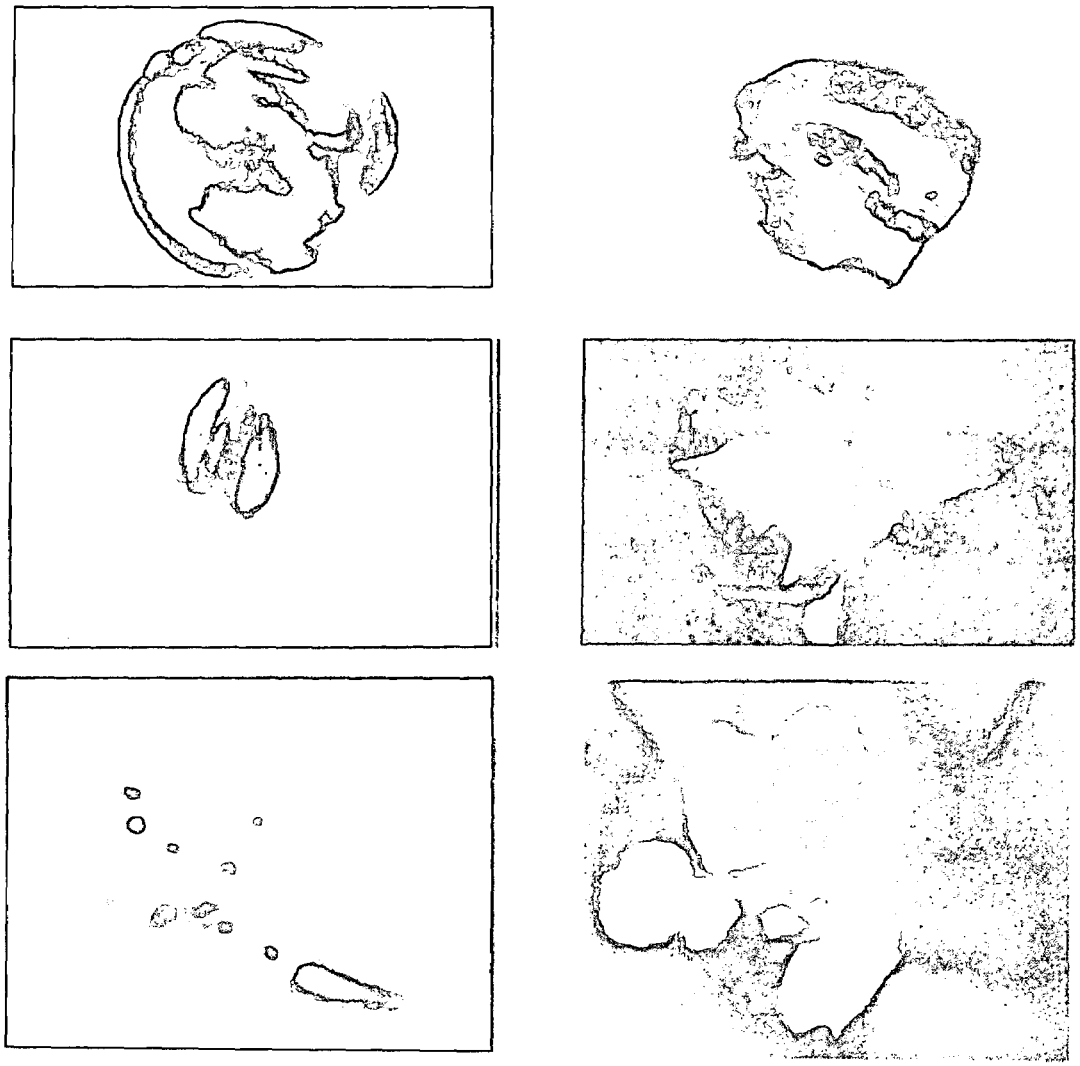
FIG. 7 shows the result of Ds-Luciferase (Ds-LUC) insertion into genes expressed in various plant organs.

A total of 1,000 plants containing independent transposition of Ds Luciferase were cultivated. Plant organs, such as seedling, flowers and fruits, were screened for Luciferase expression. The screening was done by spraying the plant tissue with 1 mM Luciferin, and subsequent imaging in total darkness. Imaging was done with a cooled CCD Princeton Instrument camera that can detect ultra-low light signals. 100 plants glowing in the dark, i.e. that express Luciferase in various tissues, were detected as depicted in FIG. 7. Out of the 1,000 plants screened, one plant expressed Luciferase in seedlings, under normal conditions, but was repressed by a cold treatment (FIG. 7, bottom panel). In order to detect very specific types of promoters or enhancers, larger populations of mutants need to be screened.

REFERENCES

Allen et al. (1993) "The Use of the Polymerase Chain Reaction and the Detection of Amplified Products" in *Methods in Molecular Biology, Vol 15: PCR Protocols: Current Methods and Applications*, B. A. White (ed.), pages 113-128, Humana Press, Totowa, N.J.

Altmann, T., Schmidt, R., and Willmitzer, L. (1992) Establishment of a gene tagging system in *Arabidopsis thaliana* based on the maize transposable element Ac. Theor. Appl. Genet. 84, 371-383.

Bechtold, N., Ellis, J. and Pelletier, G. (1993) In planta *Agrobacterium* Mediated gene transfer by infiltration of adult *Arabidopsis thaliana* plants. C. R. Acad. Sci. Paris, Sciences de la vie/Life Sciences, 316, 1194-99.

Beeckman, T., and Engler (1994) An easy technique for the clearing of histochemically stained plant tissue. Plant Mol. Biol. Rep. 12, 37-42.

Benson, Robert J., Johal, Gurmukh, Crane, Virginia C., Tossberg, John T., Schnable, Patrick S., Meeley, Robert B. and Briggs, Steven P., (1995) Cloning and characterization of the maize anl gene. The plant Cell 7: 75-84.

Bishop, G. J., Harrison, K., and Jones, J. D. G. (1996) The tomato Dwarf gene isolated by heterologous transposon tagging encodes the first member of a new cytochrome P450 family. Plant Cell 8, 959-969.

Carroll, B. J., V. I., K., Thomas, C. M., Bishop, G. J., Harrison, K., Scofield, S. R., and Jones, J. D. G. (1995) Germinal transposition of the maize element Dissociation from T-DNA loci in Tomato. Genetics 139, 407-420.

Cooley, M. B., Goldsbrough. A. P. Still, D. W., and Yoder, J. I. (1996) Site-selected insertional mutagenesis of tomato with maize Ac and Ds elements. Mol. Gen. Genet252, 184-194.

Delidow et al. 1993 "Polymerase Chain Reaction: Basic Protocols" in *Methods in Molecular Biology, Vol. 15: PCR Protocols: Current Methods and Applications*, B. A. White (ed.), pages 1-29. Humana Press, Totowa, N.J.

Dellaporta, S. L., Wood, J., and Hicks. J. B. (1983) A plant DNA minipreparation: Version II. Pl. Mol. Biol. Rep. 1, 19-21.

Dooner, H. K., and Belachew. A. (1989) Transposition pattern of the maize element Ac from the bz-m2(Ac) allele. Genetics 122, 447-458.

Fedoroff, N. V. et al. (1984) Proc. Natl. Acad. Sci. USA, 81, 3825-3829.

Fedoroff, N. V., and Smith, D. L. (1993) A versatile system for detecting transposition in *Arabidopsis*. Plant J. 3, 273-289.

Feinberg, A. P., and Vogelstein, B. (1983) A technique for radiolabeling DNA restriction endonuclease fragments to high specific activity. Anal. Biochem. 132, 6-13.

Fillati, J. J., Kiser, J., Rose, R., and Comai, L. (1987) Efficient transfer of a glyphosate tolerance gene into tomato using a binary *Agrobacterium tumefaciens* vector. Biotechnology 5, 726-730.

Gde and Youssetian, Genes in Wheat. In *Progress in Plant Breeding* (Russel, GE, ed: Butterworth, 2 Co. London) pp 1-35).

Gorbunova, V., and Levy, A. A. (1997) Circularized Ac/Ds transposons: formation, structure and fate. Genetics 145, 1161-1169.

Greenblatt, I. M. (1984) A chromosome replication pattern deduced from pericarp phenotypes resulting from movements of the transposable element, Modulator, in maize. Genetics 108, 471-485.

Hedde and Kamiya, Gibberellin biosynthesis: Enzymes, genes and their regulation. Ann. Rev. Plant Physiol. Plant Mol. Biol. 48: 431-460).

Hildering, G. J., and Verkerk, K. (1965) Chimeric structure of the tomato plant after seed treatment with Ems and X-rays. In, The use of induced mutations in plant breeding. Pergamon press, pp 317-320.

Hille, J., Koornneef, M., Ramanna, M. S., and Zabel, P. (1989) Tomato: a crop species amenable to improvement by cellular and molecular methods. Euphytica 42, 1-23.

Hoekema et al. (1983) Nature, 303, 179-180.

Horsch, R. B., Fry, J. E., Hoffmann, N. L., Eichholtz, D., Rogers, S. G., and Fraley, R. T. (1985) A general and simple method for transferring genes into plants. Science 277, 1229-1231.

R. T. (1985) A general and simple method for transferring genes into plants. Science 277, 1229-1231.

Jefferson, R. A. (1987) Assaying chimeric genes in plants: The GUS gene fusion system. Plant Mol. Biol. Rep. 5, 387-405.

Jones, D. A., Thomas, C. M., Hammond-Kosack, K. E., Balint-Kurti, P. J., and Jones, J. D. G. (1994) Isolation of the tomato Cf-9 gene for resistance to *Cladosporium fulvum* by transposon tagging. Science 266, 789-792.

Jones, J. D. G., Carland, F. C., Lim, E., Ralston, E., and Dooner, H. K. (1990) Preferential transposition of the maize element Activator to linked chromosomal locations in tobacco. Plant Cell 2, 701-707.

Keddie, J. S., Carroll, B., Jones, J. D. G., and Gruissem, W. (1996) The DCL gene of tomato is required for chloroplast development and palisade cell morphogenesis in leaves. EMBO J. 15, 4208-4217.

Knapp, S., Larondelle, Y., Robberg, M., Furtek, D., and Theres, K. (1994) Transgenic tomato lines containing Ds elements at defined genomic positions as tools for targeted transposon tagging. Mol. Gen. Genet. 243, 666-673.

Koncz, C., Chua, N.-H., and Schell, J. (1992) Methods in *Arabidopsis* research. Eds. Singapore, New Jersey, London, Hong Kong: World Scientific Pub. Co.

Leutwiler, L. S., Hough-Evans, B. R., and Meyerowitz, E. M. (1984) The DNA of *Arabidopsis thaliana*. Mol. Gen. Genet. 194, 15-23.

Mamberg, R. L. (1993) Production and Analysis of Plant Mutants, Emphasizing *Arabidopsis thalama* in METHODS IN PLANT MOLECULAR BIOLOGY AND BIOTECHNOLOGY, CRC Press (Boca Raton) pp 11-28.

Mandel, M. A. and Yanofsky, M. F. (1995) Nature 377, 522-524.

McClintock, B. (1956) Mutations in maize. Carnegie Institution, Washington Yearbook 55, 323-332.

McCormick, S., Niedmeyer, J., Fry, J., Barnason, A., Horsch, K., and Fraley, R. (1986) Leaf disc transformation of cultivated tomato (*L. esculentum*) using *Agrobacterium tumefaciens*. Plant Cell Reports 5, 81-84.

Osborne, B. I., Corr, C. A., Prince, J. P., Hehl, R., Tanksley, S. D., McCormick, S., and Baker, B. (1991) Ac transposition from a T-DNA can generate linked and unlinked clusters of insertions in tomato genome. Genetics 129, 833-844.

Poehlman, J. M., BREEDING FIELD CROPS (1987) Van Nostrand Reinhold, New York ($3^{rd}$ ed).

Rick, C. M., and Yoder, J. I. (1988) Classical and moledular genetics of tomato: highlights and perspectives. Ann Rev. Genet. 22, 281-300.

Rommens, C. M. T., Rudenko, G. N., Dijkwel, P. P., Vanhaaren, M. J. J., Ouwerkerk. P. B. F., Blok, K. M., Nijkamp, H. J. J., and Hille, J. (1992) Characterization of the Ac/Ds behaviour in transgenic tomato plants using plasmid rescue. Plant Mol Biol 20, 61-70.

Rychlick et al., "Selection of Primers for Polymerase Charin Reaction", in *Methods in Molecular Biology, Vol* 15: *PCR Protocols: Current Methods and Applications*, B. A. White (ed.), pages 31-40, Humana Press, Totowa, N.J.

Schoenmakers, H. C. H., Koornneef, M., Alefs, S. J. H. M., Gerrits, W. F. M., van der Kop, D., Cherel, I., and Caboche, M. (1991) Isolation and characterization of nitrate reductase-deficient mutants in tomato (*Lycopersicon esculentum* Mill.). Mol. Gen. Genet. 227, 458-464.

Scott, J. W., and Harbaugh, B. K. (1989) Micro-Tom—a miniature dwarf tomato. Florida Agr. Expt. Sta. Circ. 370, 1-6.

Scott, L., LaFoe, D., and Weil, C. (1996) Adjacent sequences influence DNA repair accompanying transposon excision in maize. Genetics 142, 237-246.

Shalev, G., and Levy, A. A. (1997) The maize transposable element Ac induces recombination between the donor site and an homologous ectopic sequence. Genetics, 146, 1143-1151.

Sundaresan, V. (1996) horizontal spread of transposon mutagenesis: new uses for old elements. Trends in Plant Science 1, 184-190.

Sundaresan, V., Springer, P., Volpe, P., Haward, S., Dean, C., Jones, J. D. G., Ma, H., and Martienssen, R. (1995) Patterns of gene action in plant development revealed by enhancer trap and gene trap transposable elements. Genes Dev. 9, 1797-1810.

Tanksley, S. D. (1993) Linkage map of tomato (*Lycopersicon esculentum*) (2N=24). In Genetic maps: Locus Maps of Complex Genomes. (J. O'Brien, Eds) Cold Spring Harbor, N.Y.: Cold Spring Harbor Laboratory Press, pp. 6.39-6.60.

Thomas, C. M., Jones, D., English, J. J., Carroll, B. J., Bennetzen, J. L., Harrison, K., Burbidge, A., Bishop, G. J., and Jones, J. D. G. (1994) Analysis of the chromosomal distribution of transposon-carrying T-DNAs in tomato using the inverse polymerase chain reaction. Mol Gen Genet 242, 573-585.

Verkerk, K. (1971) Chimerism of the tomato plant after seed irradiation with fast neutrons. Neth. J. agric. Sci 19, 197-203.

Weide, R., Koornneef, M., and Zabel, P (1989) A simple, nondestructive spraying assay for the detection of an active kanamycin resistance gene in transgenic tomato plants. Theor. Appl. Genet. 78, 169-172.

Weigel, D. and Nilsson, O. (1995) Nature 377, 495-500.

Wisman, E., Koornneef, M., Chase, T., Lifshytz, E., Ramanna, M. S., and Zabel, P. (1991) Genetic and molecular characterization of Adh-I null mutant in tomato. Mol. Gen. Genet. 226, 120-128.

Yoder, J., Palys, J., Albert, K., and Lassner, M. (1988) Ac transposition in transgenic tomato plants. Mol. Gen. Genet. 213, 291-296.

The invention claimed is:

1. A method for selecting a mutant miniature tomato plant having a desired trait, comprising the steps of:
   (a) providing a population of miniature tomato plants, wherein said miniature tomato plants have the following characteristics: (i) reduced size in comparison to a commercial tomato plant; (ii) maturation to produce viable seeds or tubers at a plant density of at least ten-fold higher than standard growth conditions used for a commercial tomato plant of the same species; and (iii) capable of being crossed with a commercial tomato plant of the same species;
   (b) generating mutant miniature tomato plants in said miniature tomato plant population by inducing mutagenesis of said miniature tomato plants via at least one of a T-DNA and a transposon sequence to produce a mutagenized miniature tomato plant population; and
   (c) selecting a mutant miniature tomato plant having said desired trait within said mutagenized miniature tomato plant population.

2. The method of claim 1, wherein said inducing mutagenesis is via a T-DNA.

3. A mutant miniature tomato plant population wherein a miniature tomato plant of said population has the following characteristics: (i) reduced size in comparison to a commercial tomato plant; (ii) matures to produce viable seeds or tubers at a density of at least ten-fold higher than standard growth conditions used for a commercial tomato plant; (iii) capable of being crossed with a commercial tomato plant; and (iv) carries a mutation induced by inducing mutagenesis via at least one of a T-DNA and a transposon sequence.

4. A method for producing a mutant population of a miniature tomato plant comprising the steps of:
   (a) providing a population of miniature tomato plants, wherein said miniature tomato plants have the following characteristics: (i) reduced size in comparison to a commercial tomato plant; (ii) maturation to produce viable seeds or tubers at a plant density of at least ten-fold higher than standard growth conditions used for a commercial tomato plant; and (iii) capable of being crossed with a commercial tomato plant; and
   (b) generating mutant tomato plants in said miniature tomato plant population by inducing mutagenesis of said miniature tomato plants via at least one of a T-DNA and a transposon sequence to produce said mutant population of said miniature tomato plant.

5. The method of claim 4, wherein said inducing mutagenesis is via a T-DNA.

6. The method of claim 5, wherein said miniature tomato plants are infected with *Agrobacterium*, thus producing multiple transformants wherein each transformant contains a T-DNA insertion in a different genomic position.

* * * * *

```
                           SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ggatagtggg attgtgcgtc                                              20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
ggatgatttg ttggggttta                                              20

<210> SEQ ID NO 3
<211> LENGTH: 16
<212> TYPE: DNA
<213> ORGANISM: Artificial sequence
<220> FEATURE:
<223> OTHER INFORMATION: EX1

<400> SEQUENCE: 3
gcgtgacgcc gtgacc                                                  16

<210> SEQ ID NO 4
<211> LENGTH: 16
<212> TYPE: DNA
<213> ORGANISM: Artificial sequence
<220> FEATURE:
<223> OTHER INFORMATION: EX2

<400> SEQUENCE: 4
gcgtgacggc gtgacc                                                  16
```